(12) United States Patent
Smith et al.

(10) Patent No.: US 12,239,820 B2
(45) Date of Patent: Mar. 4, 2025

(54) CARTRIDGE UNIT FOR A DRUG DELIVERY DEVICE

(71) Applicant: Sanofi, Paris (FR)

(72) Inventors: Hugh Smith, Warwick (GB); Steven Wimpenny, Warwick (GB)

(73) Assignee: Sanofi, Paris (FR)

( * ) Notice: Subject to any disclaimer, the term of this patent is extended or adjusted under 35 U.S.C. 154(b) by 949 days.

(21) Appl. No.: 17/258,785

(22) PCT Filed: Jul. 15, 2019

(86) PCT No.: PCT/EP2019/068972
§ 371 (c)(1),
(2) Date: Jan. 8, 2021

(87) PCT Pub. No.: WO2020/016163
PCT Pub. Date: Jan. 23, 2020

(65) Prior Publication Data
US 2021/0290848 A1    Sep. 23, 2021

(30) Foreign Application Priority Data
Jul. 18, 2018 (EP) ..................................... 18305978

(51) Int. Cl.
*A61M 5/24* (2006.01)

(52) U.S. Cl.
CPC ....... *A61M 5/24* (2013.01); *A61M 2005/2488* (2013.01)

(58) Field of Classification Search
CPC .. A61M 2005/2485; A61M 2005/2488; A61M 5/3135; A61M 2005/2433;
(Continued)

(56) References Cited

U.S. PATENT DOCUMENTS 9,173,995 B1 * 11/2015 Tucker ................ A61M 5/1408
9,242,040 B2 *  1/2016 Liscio ............... A61M 5/31565
(Continued)

FOREIGN PATENT DOCUMENTS

EP    1423079    7/2006
EP    2043708   12/2010
(Continued)

OTHER PUBLICATIONS

PCT International Preliminary Report on Patentability in International Application No. PCT/EP2019/068972, dated Jan. 19, 2021, 9 pages.
(Continued)

*Primary Examiner* — Nathan R Price
*Assistant Examiner* — Kayla M. Turkowski
(74) *Attorney, Agent, or Firm* — Bond, Schoeneck & King, PLLC

(57) ABSTRACT

A cartridge unit for a drug delivery device is provided, comprising: a cartridge unit guide feature, the cartridge unit guide feature being provided to mechanically cooperate with a housing guide feature provided on a housing to establish a guiding interface in order to guide relative movement of the cartridge unit and the housing when attaching the cartridge unit to the housing, wherein the cartridge unit guide feature is provided with at least one cartridge unit interface feature, wherein the cartridge unit interface feature is adapted to establish a further interface with the housing.

17 Claims, 6 Drawing Sheets

(58) Field of Classification Search
CPC .. A61M 2005/2411; A61M 2005/2444; A61M 2005/2496; A61M 2005/2492; A61M 5/347; A61M 2205/6045; A61M 5/24; A61M 5/34; A61J 1/06; A61J 1/062; A61J 1/065
See application file for complete search history.

(56) References Cited

U.S. PATENT DOCUMENTS

| | | |
|---|---|---|
| 2006/0027233 A1 | 2/2006 | Zierenberg et al. |
| 2010/0152657 A1* | 6/2010 | Steenfeldt-Jensen ........ A61M 5/31548 604/407 |
| 2011/0131777 A1 | 6/2011 | Nanjo |
| 2013/0211326 A1 | 8/2013 | Dasbach et al. |
| 2014/0012208 A1* | 1/2014 | Plumptre .......... A61M 5/31528 604/207 |
| 2017/0196770 A1 | 7/2017 | Klintenstedt et al. |
| 2018/0228976 A1* | 8/2018 | Gazeley ............ A61M 5/31541 |
| 2020/0016328 A1* | 1/2020 | Cane' ................. A61M 5/1452 |

FOREIGN PATENT DOCUMENTS

| | | |
|---|---|---|
| JP | 2007-522900 | 8/2007 |
| JP | 2013-524909 | 6/2013 |
| JP | 2013-534831 | 9/2013 |
| JP | 2013-542807 | 11/2013 |
| JP | 2014-513600 | 6/2014 |
| WO | WO 2011/032883 | 3/2011 |
| WO | WO 2011/131775 | 10/2011 |
| WO | WO 2011/131777 | 10/2011 |
| WO | WO 2011/131783 | 10/2011 |
| WO | WO 2012/064258 | 5/2012 |
| WO | WO 2012/130704 | 10/2012 |
| WO | WO 2016/065220 | 4/2016 |
| WO | WO 2016/091554 | 6/2016 |
| WO | WO 2016/150900 | 9/2016 |
| WO | WO 2017/186435 | 11/2017 |

OTHER PUBLICATIONS

PCT International Search Report and Written Opinion in International Application No. PCT/EP2019/068972, dated Aug. 20, 2019, 13 pages.

* cited by examiner

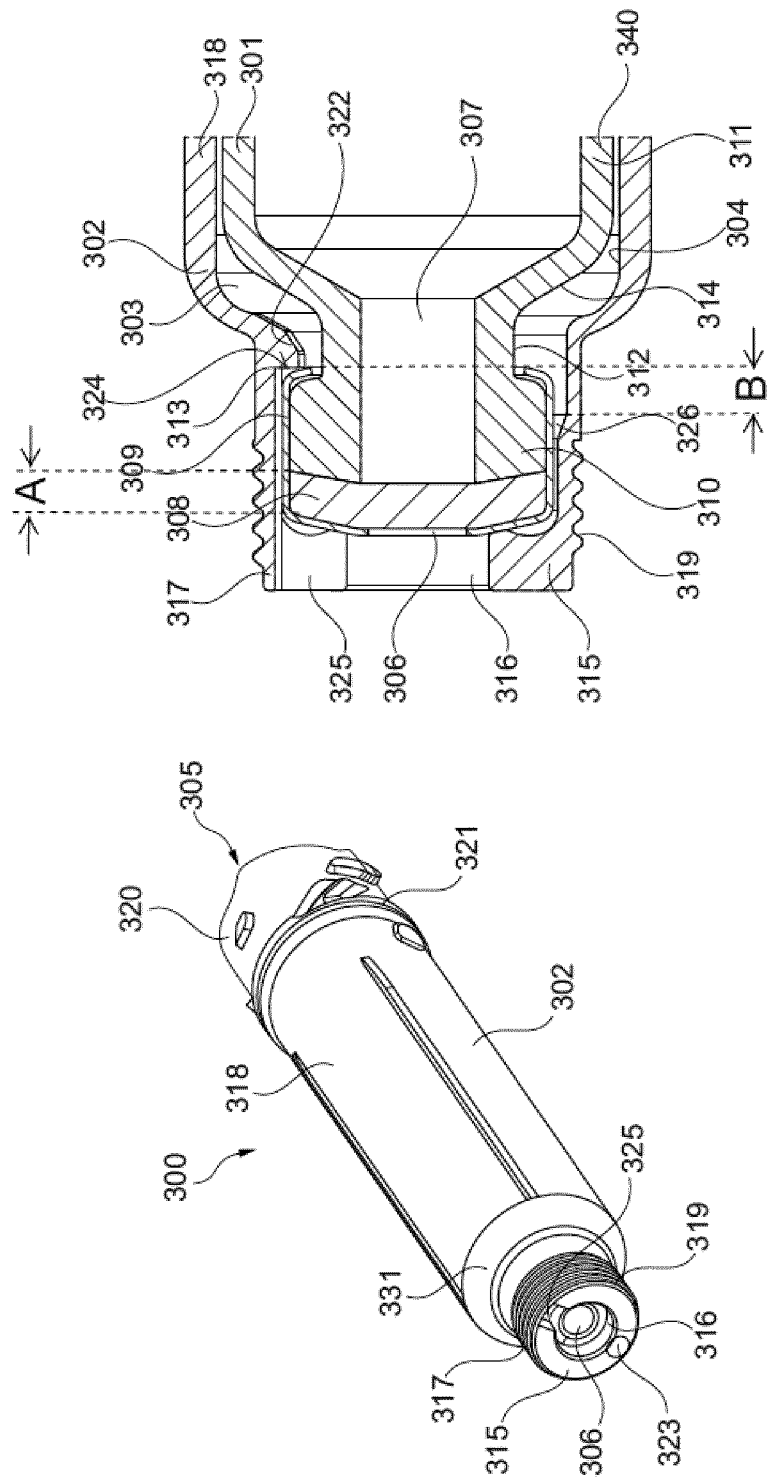

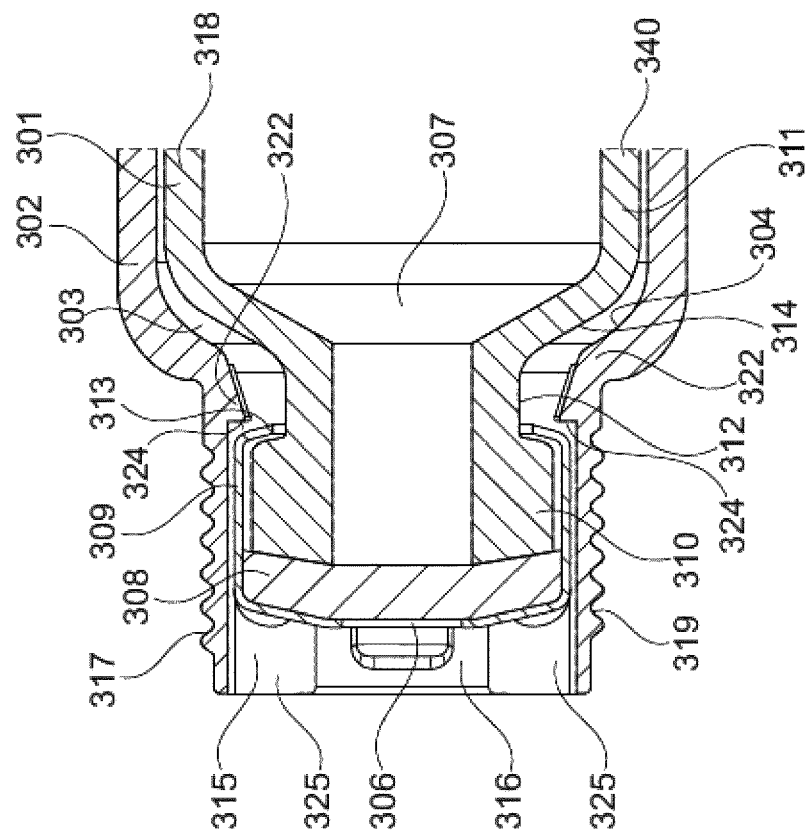
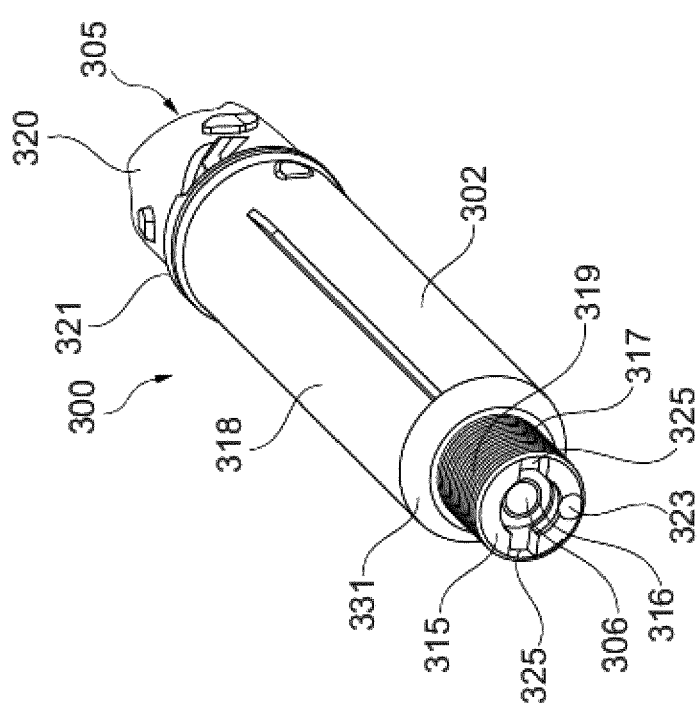
Fig. 2B
Fig. 2A

000
CARTRIDGE UNIT FOR A DRUG DELIVERY DEVICE

CROSS-REFERENCE TO RELATED APPLICATIONS

The present application is the national stage entry of International Patent Application No. PCT/EP2019/068972, filed on Jul. 15, 2019, and claims priority to Application No. EP 18305978.1, filed on Jul. 18, 2018, the disclosures of which are incorporated herein by reference.

TECHNICAL FIELD

This disclosure relates to a cartridge unit for a drug delivery device, preferably an injection device and/or a pen-type device, such as a pen-type injector.

BACKGROUND

In regular drug delivery devices, where a single drive mechanism which may be housed in a housing of the drug delivery device is used in conjunction with several cartridges or ampules to dispense drug or medicament contained in the cartridge or ampule from the device, usually a cartridge holder of the device is releasably connected or attached to the housing and can be removed or detached from the housing to replace a used cartridge. For doing so, the cartridge holder is disconnected from the housing, the used cartridge is removed from the holder and replaced with a new cartridge which is inserted into the cartridge holder, where the cartridge holder is again attached to the housing and the device is ready to be used again to dispense drug or medicament from the new cartridge.

Devices of this kind, however, do have several risks. For example, a cartridge containing a drug or medicament for which the mechanism of the drug delivery device is not specifically designed, i.e. a wrong drug, can be inserted into the cartridge holder and the user does not realize that he has put the wrong drug cartridge into the cartridge holder. This mistake may be lethal for the user and is also likely to occur as cartridges with different drugs or medicaments usually look pretty much alike. Furthermore, the cartridge, if sold as a separate item, is usually easily damaged, in particular as the standard cartridges are usually glass cartridges.

SUMMARY

Certain aspects provide improvements related to cartridge units for drug delivery devices.

An aspect of the present disclosure relates to a cartridge unit, in particular for a drug delivery device. The cartridge unit comprises a cartridge unit guide feature. The cartridge unit guide feature is expediently provided to mechanically cooperate with a housing guide feature provided on a housing, e.g. to establish a guiding interface in order to guide relative movement of the cartridge unit and the housing when attaching the cartridge unit to the housing and/or when removing the cartridge unit from the housing, such as by disconnecting the cartridge unit and the housing. The cartridge unit may be connected to the housing to form a drug delivery device. The housing may retain or house a dose setting mechanism and/or drive mechanism which is provided to set a dose of drug to be delivered and/or drive dispensing of a drug, expediently the previously set dose, from the cartridge unit. The size of the dose may be variable and/or user-settable.

The cartridge unit further comprises a cartridge unit interface feature. The cartridge unit interface feature is expediently adapted to establish a further interface with the housing. The further interface may be an additional interface in addition to the guiding interface. The further interface may be established by mechanical cooperation of a housing interface feature of the housing with the cartridge unit interface feature. The further interface may be established before and/or simultaneously with the guiding interface, particularly when attaching the cartridge unit to the housing. The further interface provides the possibility to equip the cartridge unit with another functionality such as for example a coding functionality. That is to say the further interface may be a codeable interface. By means of coding, e.g. mechanically coding or dedicating, the cartridge unit to a specific housing and/or the drive mechanism retained in the housing it can be ensured that only correct pairs of drive mechanisms and cartridge units can be connected to one another. The drive mechanisms may be designed for a specific cartridge unit, e.g. taking into account the dimensions of a cartridge of the cartridge unit, the drug or medicament and/or the drug or medicament formulation contained in the cartridge unit. By means of the coding, it can be guaranteed that only cartridge units which have a matching coding structure which may be formed by the interface feature(s) can be attached to a particular housing, whereas cartridge units with a non-matching coding structure cannot be attached to the particular housing. Thus, dedicated or coded pairs of cartridge unit and housings with matching coding structures may be connected only to one another but not crosswise.

The cartridge unit guide feature may be provided with the cartridge unit interface feature. Thus, the interface feature may be provided in a section of the cartridge unit which is already involved in guiding movement, e.g. on the cartridge unit guide feature. Accordingly, the interface feature is arranged in a section of the cartridge unit, where a guide feature is included. Manufacturing of the cartridge unit is facilitated, e.g. as only minor modifications in molding tools must be made in regions which have a functional structure. Furthermore, regular guide features such as protrusions or lugs are usually comparatively small features. By integrating the further interface feature on the guide feature, it can be achieved that a user which intends to connect a cartridge unit to a housing does not realize, whether the cartridge unit is dedicated to the housing until he realizes that the connection is possible or not by attempting to connect the unit and the housing. Thus, cartridge units with, aside from the region of the cartridge unit guide feature where the interface feature is arranged, the same dimensions and/or configurations can be used for different drugs or medicaments or drug or medicament formulations and/or cartridges of different dimensions, e.g. cartridges with different inner or outer diameters, lengths and/or volumes. This increases the users confidence in the cartridge unit as he is familiar with the general external geometry of the cartridge unit already, even if two cartridge units contain different drugs or drug formulations and/or have cartridges with different dimensions.

In an embodiment, the cartridge unit interface feature is provided on a radially facing surface, e.g. an outer surface, of the cartridge unit guide feature. The cartridge unit interface feature may be restricted to the radially facing surface. That is to say, it may not protrude over the radially facing surface, particularly preferably neither axially nor angularly. Thus, only minor modifications are necessary in a molding tool to define the interface feature in a region which defines a guide feature anyway.

In an embodiment, a plurality of cartridge unit interface features are provided on the cartridge unit guide feature.

In an embodiment, the cartridge unit comprises a plurality of cartridge unit guide features. All of these guide features, only some of these guide features or only one of these guide features may be provided with the cartridge unit interface feature. The cartridge unit guide features may be axially aligned and/or angularly separated.

In an embodiment, the cartridge unit comprises a cartridge unit coding structure which is formed by the cartridge unit interface feature(s).

In an embodiment, the cartridge unit interface feature is a protrusion or a recess, e.g. on the radially facing surface of the cartridge unit guide feature.

In an embodiment, the cartridge unit guide feature is radially oriented. Particularly, the cartridge unit guide feature may be a radially oriented protrusion. That is to say, the guide feature may have a free end facing in the radial direction, i.e. a free radial end.

In an embodiment, the cartridge unit interface feature extends along the cartridge unit guide feature. The cartridge unit interface feature may extend axially and/or angularly along the cartridge unit guide feature. Specifically, the cartridge unit interface feature may extend helically along the cartridge unit guide feature.

In an embodiment, the cartridge unit interface feature is a separate feature, in particular separate from the cartridge unit guide feature. Specifically, different surfaces may be involved in establishing the further interface and the guiding interface. The further interface may be established by surfaces of the interface feature, whereas the guiding interface is established by surfaces of the guide features.

In an embodiment, the cartridge unit guide feature comprises one or more guiding surfaces. The respective guiding surface is provided to mechanically cooperate with corresponding surfaces of the housing guide feature while the guiding interface is established and/or when the cartridge unit is attached to the housing, e.g. to define a rotational stop in an end position of the cartridge unit relative to the housing. Preferably, any one of, any arbitrarily selected plurality of, or all of the following apply:

At least one guiding surface is an axially facing surface, such as a proximally facing surface or a distally facing surface. In the following, axially facing surfaces may also be designated as axial surfaces. Further surfaces may be designated similarly by referring to the direction into which they face. For example, distally facing surfaces may be designated as distal surfaces and so on.

At least one guiding surface is an angularly or azimuthally facing surface.

If a plurality of angularly and/or axially facing surfaces are provided as guiding surfaces these surfaces face preferably in opposite axial or angular directions.

The cartridge unit interface feature is radially offset, axially offset and/or angularly offset from the one or more guiding surfaces. The cartridge unit interface feature may be angularly offset from any angularly facing guiding surface, and/or axially offset from any axially facing guiding surface.

In an embodiment, the cartridge unit interface feature is angularly restricted to the region between two angularly facing surfaces of the cartridge unit guide feature. The two angularly facing surfaces of the cartridge unit guide feature may face in opposite angular directions. The surfaces may delimit the angular extension of the guide feature. Alternatively or additionally, the cartridge unit interface feature may be axially restricted to the region between two axially facing surfaces of the cartridge unit guide feature. The two axially facing surfaces may face in opposite axial directions and/or delimit the axial extension of the cartridge unit guide feature. The respective angular surface which delimits the cartridge unit interface feature may be angularly offset from the respective surface which delimits the cartridge unit guide feature angularly. The respective axial surface which delimits the cartridge unit interface feature may end flush with the axial surface delimiting the cartridge unit guide feature in the same axial direction or be axially offset from that axial surface. One or both of the respective surfaces of the cartridge unit guide feature between which the cartridge unit interface feature is arranged or is flush with, either axially and/or angularly facing surfaces, may be guiding surfaces.

In an embodiment, the further interface is a temporary interface. Accordingly, the further interface may be established only during a limited stage when the guiding interface is established. Accordingly, when the guiding interface guides movement of the cartridge unit, there may be a stage where the further interface is established and a stage where it is not. Preferably, the further interface is not established or released in an end position which the cartridge unit has relative to the housing. Thus, the user has early certainty, whether the cartridge unit and the housing have matching coding structures—attaching the cartridge unit to the housing works—or non-matching coding structures—attaching is blocked during or before the first stage which may be known to the user as one of the stages necessarily occurring during attachment. The cartridge unit guide feature may angularly abut an angular surface of the housing guide feature when the end position has been reached.

In an embodiment, the guiding interface defines two different stages of movement of the cartridge unit relative to the housing, a first stage and a second stage. The first stage may precede the second stage when attaching the cartridge unit to the housing. The further interface may be established during or in the first stage and not be established in the second stage. Accordingly, the further interface may be a temporary interface during the timespan when the guiding interface is operative. As the further interface is established during or in the first stage, it can be guaranteed, that the user is very soon provided with information whether the cartridge unit does not match the housing to which he attempts to attach the cartridge unit. If the cartridge unit and the housing match, the further interface is established only during a limited timespan such that the further interface can be easily integrated into a standard guiding or connection mechanism such as a bayonet connection mechanism without requiring severe adjustments to the mechanism.

The first stage may comprise axial and/or angular movement of the cartridge unit relative to the housing. The first stage of movement may comprise axial movement of the cartridge unit towards the housing and angular movement of the cartridge unit relative to the housing or only axial movement towards the housing. That is to say, the first stage may comprise a helical movement. The second stage may comprise an angular movement, e.g. only angular movement or axial movement and angular movement. The angular movement during the first and second stage may be in the same rotational or angular direction. The second stage may comprise axial movement of the cartridge unit away from the housing. That is to say the axial direction in or during the second stage may be opposite to the axial direction in or during the first stage. Particularly, the second stage may comprise a helical movement, where the helixes during the first and second stage may be oppositely handed. The axial movement during the second stage has several advantages.

Firstly, the movement in the opposite axial direction during the second stage may occur right before the end of the attachment procedure. Accordingly, as this movement is notable for the user, the user may gain confidence that he has attached the cartridge unit correctly. Furthermore, the axial movement in the opposite axial direction may assists in providing a defined initial position for the drug delivery such that already the first dose of drug or medicament which is dispensed from the device can be dispensed accurately and a priming operation can be avoided. Further, the movement in the opposite axial direction may be used to reestablish an operational connection between two or more elements of the dose setting and/or drive mechanism of the drug delivery device. Such a connection may be required to deliver already the first dose accurately.

In an embodiment, the further interface is a helical interface. That is to say, when the further interface is established, the cartridge unit performs a helical movement relative to the housing. The lead of the helical interface or the helical movement of the further interface may be equal to the lead of a helical movement of the cartridge unit relative to the housing during the first stage. Thus, a helix angle, a lead, a slope and/or a pitch of the helix along which the cartridge unit interface feature and/or the housing interface feature extends may correspond to a helix angle, a lead, a slope and/or a pitch of the helical movement defined by cooperation of the cartridge unit guide feature and the housing guide feature. For example, the cartridge unit interface feature and the housing guide feature may define or extend along helixes, in particular helixes of the same helical orientation or hand, of corresponding or equal helix angles, leads, slopes and/or pitches.

In an embodiment, the cartridge unit comprises a cartridge holder and/or a cartridge. The cartridge is expediently arranged within the cartridge holder. The cartridge may contain a drug or medicament. A proximal end of the cartridge may be closed by a movable bung or piston.

Provided that fluid communication between the interior of the cartridge and the exterior is established such as by a needle piercing a septum at the distal end of the cartridge, and the bung is displaced in the distal direction with respect to the cartridge towards an outlet of the cartridge, drug or medicament may be dispensed from the cartridge. The cartridge unit guide feature may be provided on an exterior surface of the cartridge holder, e.g. a side wall of the cartridge holder. The cartridge unit guide feature may be provided in a proximal section of the cartridge holder. The proximal section may be received in the housing when the cartridge holder and the housing have been connected.

In an embodiment, the cartridge unit is a cartridge assembly. The cartridge assembly comprises the cartridge and the cartridge holder. The cartridge is, preferably permanently and/or irreleasably, secured in the cartridge holder of the cartridge assembly. Therefore, the cartridge holder may provide additional protection for the cartridge. Further, standard cartridges, e.g. of 1.5 mL or 3.0 mL volumes, may be used even for different drugs or medicaments, without having to modify the cartridge structure for coding purposes. The cartridge assemblies may be assembled by the manufacturer and distributed. The adjustments to the different housings, drive mechanisms, interfaces and/or codings may be effected by using different cartridge holders.

The cartridge assembly may be a single disposable item. Accordingly, the cartridge assembly comprising the holder and the cartridge retained therein may be a consumable item.

In an embodiment, the guiding interface is a standard interface. Accordingly, in different cartridge units, the guide features may be formed alike. The only differences may be in the interface features. Thus, the general connection or guiding mechanisms may operate alike in all of the drug delivery devices of a set or an arrangement of devices, the housing of each device being connectable only to the cartridge unit with the matching coding structure. In the set the matching coding structures of pairs of housings and cartridge units may be unique.

In an embodiment, the cartridge unit comprises a plurality of cartridge unit interface features. The cartridge unit interface features may be arranged or provided on the cartridge unit guide feature. The cartridge unit interface features may be formed alike. The cartridge unit interface features may be uniformly distributed in the angular direction. The cartridge unit interface features may be oriented along one another. For example, they may be adjusted to guide the same type of movement such as a helical movement, e.g. of the same lead or helix angle.

In an embodiment, the guiding interface is a bayonet-type interface. That is to say, the interface may define or guide two different types of movement, e.g. one at least predominantly axial movement, e.g. during the first stage, and one at least predominantly rotational or angular movement, e.g. during the second stage.

Another aspect relates to a set comprising two different cartridge units as described previously, i.e. a first cartridge unit and a second cartridge unit. The first cartridge unit and the second cartridge unit preferably differ in the configuration and/or arrangement of their cartridge unit interface features. Specifically, a first coding structure formed by the cartridge unit interface feature(s) of the first unit and a second coding structure formed by the by the cartridge unit interface feature(s) of the second unit may be different. Aside from the interface features, the cartridge holders of the units may be structurally and/or dimensionally formed alike. The first and second cartridge unit may contain different drugs or medicaments or drug formulations or medicament formulations and/or the first and second cartridge unit may comprise cartridges of different dimensions, e.g. lengths, diameters, and/or filling levels or inner volumes. The set may comprise a third cartridge unit which has the same drug or drug formulation as one of the first and second cartridge units and/or a cartridge of the same dimensions as one of the first and second cartridge units. The third cartridge unit may have the same configuration including the interface feature (s) as that cartridge unit which contains the same drug or drug formulation and/or the cartridge of the same dimension, e.g. the first cartridge unit. The difference in the interface features between the units is so prominent that the first and second cartridge units cannot be attached to the same housing, which has a housing coding structure which matches only one of the cartridge unit coding structures of the first and second cartridge unit. The third cartridge unit and the first cartridge unit may be attachable to the same housing, whereas the second cartridge unit is not attachable to this housing.

In the present context different drugs or medicaments may mean that the cartridge units contain drugs or medicaments based on different active pharmaceutical ingredients. Different drug or medicament formulations may mean that the formulations may be based on the same active pharmaceutical ingredient but the cartridges comprise liquid with different concentrations of the active pharmaceutical ingredient, for example.

In an embodiment, the first cartridge unit and the second cartridge unit have cartridge unit guide features of the same configuration and/or arrangement. These cartridge unit guide features may be adjusted to one another and be configured to establish according guiding interfaces when connected with different housings. The relative movements between cartridge units and housings may be the same, e.g. with respect to angular and/or axial distances. The different cartridge unit interface features or coding structures of the two cartridge units establish different further interfaces which may prevent that both units can be attached to the same housing.

In an embodiment, the two different cartridge units comprise cartridges of different length, diameter, and/or volume. Therefore, the cartridges may contain different amounts of liquid and/or different concentrations of the same drug or medicament.

In an embodiment, the cartridge unit interface features of the two cartridge units are adjusted to helical interfaces of the same lead. Accordingly, the lead of a helical interface established by the cartridge unit interface feature of the first cartridge unit and the lead of a helical interface established by the cartridge unit interface feature of the second cartridge unit may be equal. Nevertheless, the interface features may be configured and/or arranged differently.

In an embodiment, the cartridge holder of the first cartridge unit, the cartridge holder of the second cartridge unit, and/or the cartridge holder of the third cartridge unit have the same exterior dimension and/or shape.

In an embodiment, the width, particularly the angular width, the number, and/or the pitch, e.g. the angular pitch, of the interface features of different cartridge units, particularly of the first cartridge unit and the second cartridge unit, are different. Thus, by means of varying width, number, and/or pitch, between cartridge units with cartridges with different drugs or medicaments, drug or medicament formulations, volumes, lengths and/or diameters, the coding may be effected. Regardless of width, number, and pitch, the movement of different cartridge units and also of the first and second cartridge unit when being attached to a housing with a matching coding structure may be the same as it is governed by the guiding interface, which may be configured in the same way for all of the cartridge units. The width, number and/or the pitch of the cartridge unit interface features of the third cartridge unit may be equal to one of the other cartridge units, expediently to the one with the same drug or medicament or drug or medicament formulation and/or a cartridge of the same dimension.

Another aspect relates to a drug delivery device. The drug delivery device expediently comprises a housing. A dose setting and/or drive mechanism may be retained in the housing. The mechanism may comprise a piston rod and or a dose setting member. The piston rod may be arranged to drive a bung which is moveably retained in a cartridge. The drug delivery device further comprises a cartridge unit, preferably one as previously described. The cartridge may be part of the cartridge unit. The cartridge unit is, preferably releasably, attached to the housing.

In an arrangement of two different drug delivery devices as explained above, which comprise cartridge units containing different drugs or drug formulations and/or cartridges of different dimensions, the cartridge unit of any one of the drug delivery devices cannot be assembled to the housing of the other drug delivery device due to different cartridge unit interface features and/or housing interface features.

In another arrangement of two different drug delivery devices as explained above, the cartridge units of any one the devices can be disconnected from the housing of device and connected to the housing of the other drug delivery device. These two cartridge units expediently comprise the same drug or drug formulation and/or cartridges of the same dimensions, e.g. length, diameter, and/or volume. The two devices preferably also comprise identical cartridge unit interface features and/or housing interface features.

The terms "distal" and "proximal" as used herein may refer to opposite axial directions or ends. "Distal" may refer to a direction towards the dispensing end or an end of a component of a drug delivery device which is or is to be arranged closest to the dispensing end of the cartridge, the cartridge holder, the cartridge unit or the drug delivery device. "Proximal" may refer to a direction away from the dispensing end or an end which is or is to be arranged further away from the dispensing end of the cartridge, the cartridge holder, the cartridge unit or the drug delivery device.

The terms "axial", "radial", "angular", or "azimuthal" as used herein may be used with respect to a main longitudinal axis of the device, the cartridge unit, the cartridge, the housing or the cartridge holder, e.g. the axis which extends through the proximal and distal ends of the cartridge unit, the cartridge, the cartridge holder or the drug delivery device.

Features disclosed above in conjunction with the cartridge unit, the set or the drug delivery device should not be regarded as referring to only the recited aspect or embodiment. Rather, the features also apply for other embodiments or aspects. Features disclosed in conjunction with the assembly do also apply for the device and vice versa. Of course, features disclosed in specific embodiments, be it above or further below, can also be applied in combination with one another and/or with other features of other embodiments.

BRIEF DESCRIPTION OF THE FIGURES

Further features, advantages and advantageous embodiments of the present disclosure will become apparent from the following description of the exemplary embodiments in conjunction with the drawings.

FIGS. 1A through 1F illustrate an embodiment of a cartridge assembly on the basis of a schematic perspective view in FIG. 1A and a schematic sectional view of the assembly in FIG. 1B, and different views of the cartridge holder without the cartridge being arranged therein in FIGS. 1C through 1F.

FIGS. 2A and 2B illustrate one embodiment of a cartridge assembly as cartridge unit on the basis of an oblique view in FIG. 2A and a schematic sectional view in FIG. 2B.

DETAILED DESCRIPTION

Figure 1C:
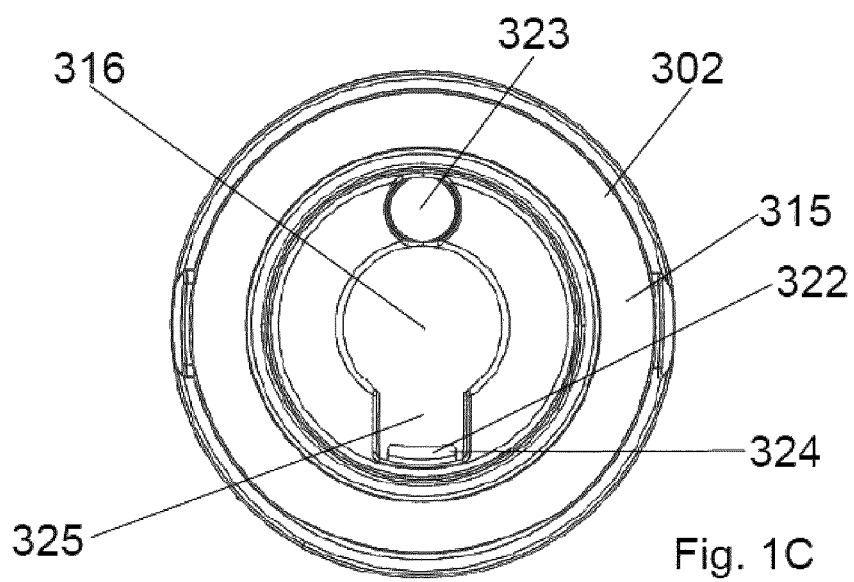
Figure 1D:
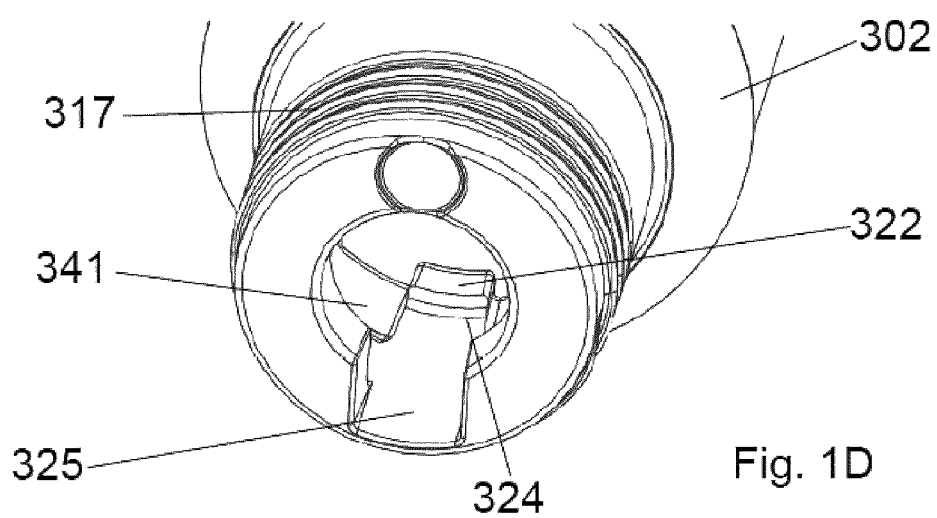
Figure 1E:
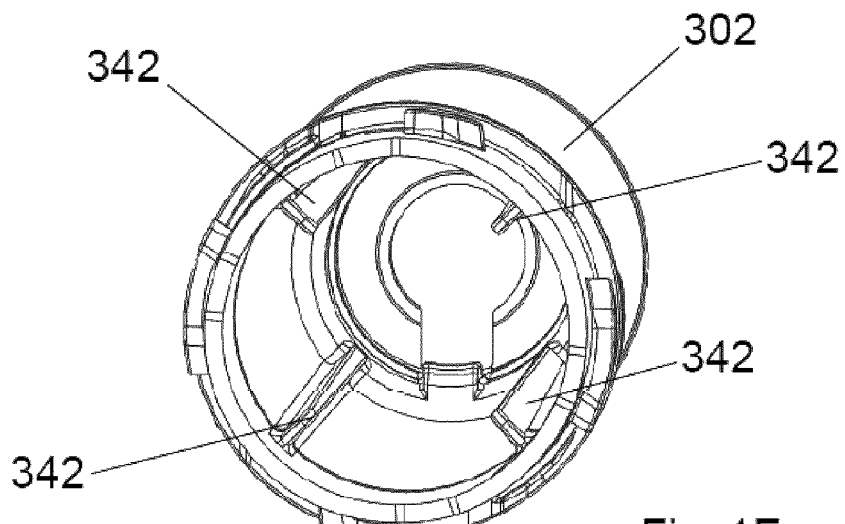

Identical elements, elements of the same kind and identically acting elements may be provided with the same reference numerals throughout the figures.

In the following, in conjunction with the FIGS. 1A through 2B, embodiments of cartridge assemblies as cartridge units are disclosed. In each case, fixing features are integrated into the cartridge holder of the unit. Before the specifics of the respective embodiments are disclosed, features which may apply to all embodiments are discussed. FIGS. 1A through 1F, as well as 2A and 2B each illustrate one embodiment of a cartridge assembly. The figure denoted with "A", in each case shows a schematic perspective view of the cartridge assembly, where in the figure denoted with "B" only the distal region, i.e. the part of the assembly close to its distal end, is shown.

The cartridge assembly 300 comprises a cartridge 301 and a cartridge holder 302. The cartridge 301 is arranged within a cartridge holding or retaining section 303 of the cartridge holder. The cartridge retaining section is expediently delimited by an inner wall 304 of the cartridge holder 302, preferably circumferentially. The cartridge holder 302 has an opening 305. The opening 305 is expediently a proximal opening. The proximal opening may provide access to the interior of the cartridge holder from the proximal end of the holder. Via the opening 305, the cartridge 301 can be inserted into the cartridge holder. A dispensing end 306 of the cartridge may be inserted or introduced into the cartridge through the opening 305. The opposite end of the cartridge holder is the distal end of the cartridge holder 302, which may be that end which is arranged closest to the dispensing end 306 of the cartridge 301. The distal end of the cartridge holder is preferably designed to retain the cartridge in the holder, e.g. by abutment, such that the cartridge may only leave the cartridge holder through the opening 305. The axial extension of the cartridge holder is expediently chosen so as to cover at least 50%, preferably more than 60% or more than 70% such as more than 80% or more than 90% of the total length of the cartridge. The entire cartridge may be covered by the cartridge holder 302 as depicted in the embodiments.

The end of the cartridge opposite to the dispensing end 306, i.e. the proximal end, is not illustrated explicitly in the figures. This end may be closed by a movable bung or stopper, which is likewise not explicitly illustrated. The bung or stopper may sealingly close a proximal opening of the cartridge. A drug or medicament 307 is contained in that region of the cartridge which is arranged between the dispensing end and the bung. Drug or medicament may be dispensed through the dispensing end 306 from the cartridge, if fluid communication between the interior of the cartridge and the exterior is provided and the bung is moved towards the dispensing end. The amount of drug 307 or medicament in the cartridge is preferably sufficient for a plurality of doses, where the size of the dose may be set by the user or may be fixed, e.g. by the design of the drive mechanism used to deliver the drug from the drug delivery device which comprises the cartridge.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

On the side of the dispensing end 306, the interior of the cartridge which holds the drug 307 or medicament is sealingly closed by a septum 308. The septum 308 may be retained at or fixed relative to a cartridge body 340 of the cartridge by means of a septum retainer 309. The septum 308 is expediently pierceable, e.g. via a needle, which may provide fluid communication between the interior of the cartridge and the exterior. The septum retainer 309 may be formed by a cap, e.g. a metal cap, such as an aluminum cap. The metal cap may be connected via clamping or crimping to the cartridge body 340. The body of the cartridge may be formed of glass. The body 340 may define the outer contour of the cartridge. In the region of the dispensing end 306, where the needle should penetrate the septum, an opening is provided in the septum retainer 309 to allow the needle to pass through the region of the septum retainer. The cartridge 301 comprises a head portion 310 and a main body portion 311. The head portion 310 is arranged on the side of the dispensing end 306. The main body portion 311 may be arranged closer to the proximal end of the cartridge than the head portion 310. Between the head portion 310 and the main body portion 311 a neck portion 312 may be arranged. The main body portion 311 may be that region, where the bung or stopper may travel. The main body portion has a tubular configuration. The neck portion 312 may have a reduced diameter, outer and/or inner diameter, as compared to the main body portion 311. The head portion 310 has a reduced diameter, outer and/or inner diameter, as compared to the main body portion 311. The neck portion 312 has a reduced diameter as compared to the main body portion and also with respect to the head portion 310. The diameter may be the extension of the cartridge in a direction perpendicular to the main longitudinal axis of the cartridge or the cartridge assembly which extends between the proximal end and the distal end. The neck portion may extend circumferentially. The entire cartridge 301 may be rotationally symmetric relative to the main longitudinal axis. The transition between the head portion 310 and the neck portion 312 may be formed via a comparatively steep surface, which is preferably less inclined relative to the radial direction than the surface which is provided between the neck portion 312 and the main body portion 311. Accordingly, the transition between the neck portion 312 and the main body portion 311 may be less steep than the one between the head portion 310 and the neck portion 312. Specifically, a cartridge surface 313, which may delimit the head portion 310 proximally, may have an inclination relative to the radial direction which is less than the inclination of a shoulder surface 314 which delimits the main body portion distally. The cartridge surface may be formed by the septum retainer 309 or, alternatively by the cartridge body 340. The septum retainer 309 may clamp the septum to the cartridge body. Thus, the septum retainer may extend from the distal end along the cartridge to a surface of the neck portion of the cartridge body facing away from the distal end of the cartridge and extending in the radial direction to clamp the septum 308 to the cartridge body. The cartridge may comprise or consist of the cartridge body 340, the septum 308, the septum retainer 309, the drug or medicament 307, and/or the bung (not explicitly illustrated).

The cartridge holder 302 comprises on that end opposite of the opening 305 and/or closest to the dispensing end 306 of the cartridge, i.e. its distal end, a distal end wall 315. The distal end wall may extend circumferentially in a ring-like fashion. A proximal surface of the distal end wall 315 is arranged to abut the distal end face of the cartridge 301. In this way, the cartridge 301 can be retained in the cartridge holder without moving distally relative to the cartridge holder 302. The distal end wall 315 may define an opening 316 in the cartridge holder. The end wall may extend around the opening such that the opening is a central opening in the end wall. The opening may extend axially through the end wall 315. The opening 316 may be provided such that a needle can be guided through the opening towards the cartridge, in particular towards the septum 308.

The cartridge holder 302 may comprise a distal region 317 and a main body region 318. The distal region 317 is arranged closest to the dispensing end of the cartridge and/or to the distal end wall 315 of the cartridge holder. The main body region 318 is arranged further away from the distal end or the distal end wall 315 and/or closer to the opening 305 than the distal region. As compared to the main body region the distal region may have a reduced outer diameter. The reduction may be determined by the reduced diameter of the head portion as compared to the diameter of the main body portion of the cartridge. The main body region 318 and the distal region may be connected by an inwardly directed shoulder region 331. In the distal region a needle connector 319, for example a thread may be arranged. Via the needle connector, a needle unit, for example a hub of a needle unit may be secured to the cartridge holder 302. A needle retained in the needle hub may be guided through the opening 316, pierce the septum 308 and provide fluid communication to the interior of the cartridge to dispense drug or medicament 307 from the cartridge 301. The distal region 317 may be designed to receive the head portion 310 of the cartridge 301 in its interior. The main body region 318 may be designed to receive the main body portion 311 of the cartridge. On the side of the proximal end the cartridge holder may have a connection or interface region 320. In that region, connection or interface features may be provided, which are configured to cooperate with corresponding features on a housing 10 to connect the cartridge assembly 300 to the housing to form a drug delivery device 1 (see FIGS. 4 and 5). The connection features may be designed for a threaded or a bayonet connection between cartridge holder and housing. Preferably, the connection or interface features are coded to a housing which houses a drive mechanism designed for the drug or medicament contained in the cartridge of the cartridge assembly. The coding ensures that only a correct cartridge assembly can be assembled to the housing to form a drug delivery device. In this way, it can be guaranteed that the drug or medicament in the cartridge assembly is dispensed using a drive mechanism which is specifically designed to dispense the content of the cartridge. The drive mechanism may comprise a piston rod, which is arranged to drive the bung or stopper distally relative to the cartridge, if drug or medicament should be dispensed from the cartridge. An embodiment of a potential coding, which could be applied for the cartridge holder is discussed in more detail further below in connection with FIGS. 3A to 3D.

Between the proximal end and the distal end of the cartridge holder 302, preferably closer to the proximal end than to the distal end, a radially outwardly protruding step 321 or flange, may be provided. The step or flange 321 may extend over the entire circumference of the cartridge holder 302. A proximal surface of the step 321 may be arranged to contact a distal surface of the housing when the cartridge assembly is connected to the housing. The connection region 320 may be covered by the housing, when the assembly has been connected to the housing. The main body region 318 and the distal region 317 may, however, protrude from the housing.

Furthermore, the cartridge holder 302 comprises at least one fixing feature 322. As seen along the axial direction, the fixing feature 322 is provided between two interior regions of the cartridge holder, where one is adapted to receive and retain the head portion 310 and another one is adapted to receive and retain the main body portion 311 of the cartridge. The fixing feature 322 may extend in the region of the neck portion of the cartridge 301. The fixing feature 322 protrudes radially from an inner wall of the cartridge holder 302. Preferably, the fixing feature 322 reduces the inner diameter the cartridge holder such that in that region, the inner diameter is less than the outer diameter of the head portion of the cartridge.

Therefore, if the head portion of the cartridge should be guided axially past the fixing feature from the proximal opening, the fixing feature has to be deflected radially outwardly, e.g. displaced only radially. If the fixing feature is deflected, the head portion can pass the fixing feature. Preferably, the fixing feature is deflected by means of the head portion cooperating with a proximal surface of the fixing feature which may be oblique, i.e. neither perpendicular nor parallel, with respect to the main axis of the cartridge holder. After the head portion has passed the fixing feature, the fixing feature may move radially inward again, e.g. resiliently. The interior region of the cartridge holder which is designed to receive the head portion 310 may have a reduced diameter as compared to that region which receives the main body portion 311.

The fixing feature 322 is formed integrally, e.g. by injection molding, with a section of the cartridge holder which defines an exterior surface or at least the outer contour of the cartridge holder. That is to say, if applicable the cartridge holder may be provided with a coating on the exterior surface whereas the outer contour may still be defined by the section of the cartridge holder the fixing feature is integrated into. In FIGS. 1A through 4A, an injection gate mark 323 is shown, which indicates the position where the fluid plastic compound is injected into a mold cavity which defines the shape of the cartridge holder. The injection gate mark 323 is positioned in the region of the distal end wall 315 of the cartridge holder, particularly on a distal face of the distal end wall.

The fixing feature 322 comprises a fixing surface 324. The fixing surface 324 may be a distal surface of the fixing feature. Preferably, the fixing surface is radially oriented, i.e. it extends in the radial direction, and/or plane. The fixing surface 324 is arranged to abut or abuts a proximally facing surface of the cartridge, such as the cartridge surface 313. Thus, the cartridge surface 313 and the fixing surface 324 are arranged to prevent that the cartridge is removed proximally from the cartridge holder through the opening 305 by mechanical cooperation with one another. Accordingly, removal of the cartridge from the holder through the opening 305 is prevented by means of the fixing feature 322. The fixing feature 322 may be formed as a snap and/or clip feature. The angular extension of the fixing feature or the fixing surface may be less than or equal to one of the following values: 20°, 15°, 10°.

Furthermore, an outer wall of the cartridge holder is provided at the axial position of the fixing feature. Thus, the cartridge holder is closed at least in the region of the fixing feature. Accordingly, the fixing surface and/or the fixing feature cannot be accessed from the outside. This reduces the chances that the cartridge assembly can be tampered with.

In the following, some embodiments of cartridge holders with fixing features integrated into the cartridge holder are discussed in more detail. The embodiment depicted in FIGS. 1A and 1B, has one fixing feature 322, in particular just one. Of course, a plurality of fixing features could be provided as well. Such an embodiment is shown in FIGS. 2A and 2B which is very similar to the one of FIGS. 1A and 1B.

The fixing feature 322 protrudes radially from the inner wall 304 of the cartridge holder 302. The fixing feature 322 is arranged in the interior of the distal region 317 of the cartridge holder 302 and, particularly, in the interior region of the cartridge holder where the needle connector 319 is provided on the exterior. As is apparent from FIG. 1A and also from FIG. 1B, the distal end wall 315 which has a generally ring-like configuration, has an opening 325. The opening 325 is radially oriented and interrupts the ring defined by the distal end wall 315. The opening 325 extends radially outwardly from the opening 316. The angular and radial position of the opening 325 may correspond to the one of the fixing feature 322 or the fixing surface 324, where the opening is axially offset from the fixing feature, e.g. in the distal direction. Particularly, as seen from the distal end along the axis, the fixing surface may be visible from the distal end. The fixing surface may be framed radially and angularly by sidewalls which delimit the opening 325. In the figures, the head portion 310 of the cartridge 301 is arranged between the opening 325 and the fixing surface 324. The angular dimension and/or the radial dimension of the opening 325 may define, may correspond to or may be greater than the angular dimension and/or the radial dimension of the fixing surface and/or the fixing feature. Providing an opening in the region of the distal end facilitates molding of the cartridge holder with the integrated fixing feature with only minor modifications to the mold or molding tool as compared to a cartridge holder without fixing features. In a cartridge holder without a fixing feature, two core pins of different diameters may be used for producing the cartridge holder by injection molding, where one core pin defines the interior of the distal region and one core pin defines the interior of the main body region 318 of the cartridge holder. A short core pin may define the interior in the distal region and a long core pin may define the region of the interior in the main body region. The fixing feature 322 may be integrated right at the intersection or the boundary of the two different core pins of the injection molding tool. The opening 325 may be formed during the molding process and facilitates the molding of a cartridge holder with the fixing features 322 integrated into it. The opening 325 may be defined by a protrusion, e.g. of metal, on the short core pin.

In the region where the fixing feature is provided, e.g. the distal region 317, the cartridge holder may be radially deformable. Thus, the inner diameter may be increased when the cartridge holder is exposed to a radially outwardly directed force. The capability of the cartridge holder to be radially deformed when exposed to a radially directed force may be increased in that angular section of the distal region 317 which overlaps angularly with the opening 325. The fixing feature 322 is arranged in this region as it overlaps angularly with the opening. The fixing feature is expediently non-flexible and/or rigid, e.g. more rigid than the distal region 317 or the inner wall of the first region where the head portion of the cartridge is to be arranged. Thus, when an axial and/or radial force acts on the fixing feature, e.g. while the head portion is guided along and in contact with the fixing feature, the cartridge holder is widened on account of the rigidity of the fixing feature 322. The fixing feature itself is not deformed or flexed. After the head portion 310 has passed the fixing feature 322, the fixing feature is displaced inwardly again and the cartridge surface 313 and the fixing surface 324 are arranged as depicted in FIG. 1B. The fixing feature is preferably not deformed during this process and, in particular, not axially deflected or pivoted.

As shown in FIG. 1B, distally offset from the fixing surface 324, a sloped surface 326 (also referred to as cartridge guiding feature in the description below) which rises radially along its extension in the distal direction, is arranged. By means of this surface, which is preferably arranged at the opposite side of the fixing surface or at least angularly offset from the fixing surface, a radial movement of the head portion 310 of the cartridge 301 may be achieved to a region overlapping radially with the fixing surface 324. Thus, the sloped surface acts as a cartridge guiding feature during the assembling process of the cartridge assembly 300. References to the sloped surface 326 may therefore be regarded as references to the cartridge guiding feature and vice versa. The radial overlap of the fixing surface 324 and the surface 313 of the cartridge 301 when the cartridge has reached its final position may be increased in this way. The sloped surface 326 may strengthen the stability of the securing of the cartridge in the cartridge holder, e.g. in case only one fixing feature is provided.

The distal offset (highlighted with "B" in FIG. 1B) of the cartridge guiding feature 326 from the fixing feature, from the fixing surface 324 and/or from a radial free end of the fixing feature 322 may be greater than the thickness (highlighted with "A" in FIG. 1B) of the septum 308 of the cartridge. This ensures that the septum retainer 309 is backed by the more rigid cartridge body 340 and preferably not by the septum, when the cartridge interacts with the fixing feature 322 to radially displace the feature outwardly in order to temporarily widen the interior of the cartridge holder. Thus, the force required to displace the feature 322 is not transferred to the septum. If the force were transferred to the septum, the risk that the septum retainer 309, which may be a thin metal component, is deformed or the septum is damaged is considerably increased. This can be avoided by the distal offset between cartridge guiding feature 326 and the fixing surface 324 by more than the thickness of the septum 308. The distal offset B is expediently less than the axial extension of the head portion 310 of the cartridge. In this way, the cartridge guiding feature may properly guide the cartridge 301 radially inwardly by cooperating with the head portion 310.

In the region of the interior of the cartridge holder 302 between the cartridge guiding feature 326 and the fixing surface 324, the inner diameter of the interior of the cartridge holder may be greater than in the region of the cartridge guiding feature and/or in a region distally offset from the cartridge guiding feature, if such a region is present which it may be or may not be. In the region of the interior of the cartridge holder between the cartridge guiding feature and the fixing surface the inner diameter may be greater than the inner diameter in the fixing feature region. In the region of the cartridge guiding feature 326 and/or distally with respect to the cartridge guiding feature, the inner diameter of the cartridge holder may be greater than the inner diameter in the fixing feature region, e.g. greater than or equal to the outer diameter of the head portion 310.

In other words, the septum retainer 309 (also referred to as metal sleeve 309 in the description below) has a distal section which surrounds the soft septum 308, and a proximal section that surrounds the neck of the cartridge body or glass ampoule 340. It is advantageous if the distal section of the septum retainer has moved past the fixing surface 324 before the distal section makes contact with the cartridge guiding feature or sloped surface 326. In this way the radial overlapping of the metal sleeve 309 and the fixing surface is minimal during the period of assembly where the fixing surface could damage the metal sleeve 309, and this overlapping is only increased when the fixing surface has moved past the distal section of the metal sleeve 309 and is applying radial pressure to the proximal section. As the proximal section is supported by a harder, e.g. glass like, material than the distal section it will not be damaged or indented. The final overlapping between the fixing surface and the cartridge surface at the end of assembling process is still high. The final overlap may be defined by the smaller inner diameter of the cartridge holder in the region of the sloped surface which marks the end of the sloped surface 326.

When a cartridge holder 302 with an integrated fixing feature 322 was tested, it has been discovered, that the distal section of the septum retainer 309 dents badly unless the diameter prior to sloped surface 326 is sufficiently larger than the diameter after sloped surface 326 so that the cartridge 301 can move away from the fixing feature with minimal, if any, interference in the distal section of the septum retainer and that this interference only increases after the fixing feature is pressing in the region of the septum retainer 309 where the head portion of the cartridge body, e.g. of glass, backs up/supports the septum retainer, which may be a thin and easily deformable metal component.

When the cartridge 301 has been assembled into the cartridge holder 302, the fixing feature 322 may block proximal movement of the cartridge 301 relative to the holder 302. The fixing feature, however, expediently does not exert a securing force, e.g. a distally or radially directed force, onto the cartridge regularly but only prevents removal of the cartridge from the cartridge holder. In this way, the force load onto the cartridge may be advantageously low.

FIGS. 1C through 1F show additional views of the cartridge holder 302. FIG. 1C shows a view from the distal end. As is immediately apparent, the angular dimension of the fixing feature 322 is less than the one of the opening 325. The radial dimension of the fixing feature 322 or the fixing surface is less than the one of the opening 325 as well. From FIG. 1D, which shows the distal end as well but in a perspective view, it can be gathered that the cartridge holder, in particular the distal region 317, is reinforced, i.e. has a higher wall strength or thickness, in a region which is angularly adjacent to the fixing feature 322. A reinforcement section 341 extends circumferentially in the interior of the cartridge holder. The reinforcement section may axially overlap with the fixing feature. The reinforcement section 341 may be arranged distally offset from the fixing feature 322 alternatively or additionally. In the region of the interior of the cartridge holder which angulary overlaps with the fixing feature the reinforcement section is preferably interrupted to promote radial deformability of the cartridge holder when the head portion displaces the fixing feature 322 radially.

Figure 1F:
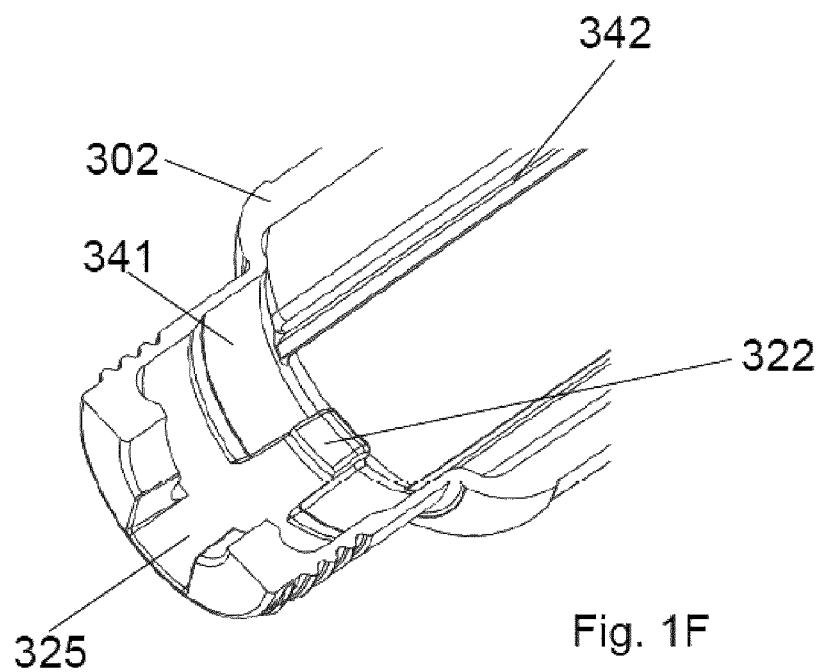

As seen from the opening 325 axially towards the fixing surface 324, the wall thickness of the holder 302 may be less than the wall thickness in the reinforcement section 341. The wall thickness of the cartridge holder 302 in the region of the fixing feature 322 and defined by the fixing feature may be greater than the one in the reinforcement section 341. The fixing feature 322 may radially protrude over the reinforcement section 341. The reinforcement section 341 is also depicted in FIG. 1F which shows a perspective sectional view of the cartridge holder 302. In this figure as well as in FIG. 1E, which shows a view from the proximal end of the cartridge holder 302, it is shown that the interior of the cartridge holder comprises a plurality of circumferentially disposed, preferably equally spaced, spacer features or cartridge support features 342, e.g. ribs. The features 342 are axially oriented. The features 342 may be provided to radially support the cartridge, e.g. the main body portion 311 thereof, if the cartridge is retained in the cartridge holder. These features may be the only difference between a cartridge holder which receives cartridges with a smaller diameter and one which receives a cartridge with greater diameter. The cartridge holder for the larger diameter cartridge may, expediently, not have the cartridge support features 342. Thus, the exterior dimensions of the cartridge holder may be the same although the exterior diameters of the cartridges retained in the cartridge holders are different.

As is apparent from the figures, e.g. from FIG. 1B, the needle connector 319, e.g. a thread, is distally offset from the fixing feature 322. Specifically, the region between the fixing feature and the cartridge guiding feature or sloped surface 326 may be free of the needle connector 319. The needle connector may axially overlap with the cartridge guiding feature 326 or be provided distally offset from this feature 326. Thus, the axial extension of the needle connector 319 may be less than in other cartridge holder designs. For example, the needle connector 319 may be restricted to a distal section of the distal region 317 of the cartridge holder, where between the needle connector 319 and the main body region a connector-free region is arranged. The axial extension of the connector-free region may be greater than 50% of the axial extension of the distal section with the needle connector. The axial extension of the distal section with the needle connector may be greater than the one of the connector-free region. As the cartridge holder in the region between the fixing feature 322 and the guiding feature 326 has a reduced wall thickness to increase the inner diameter of the cartridge holder 302, e.g. in order to maintain a given outer contour or dimension of the cartridge holder 302, providing an additional radial indentation on the exterior in this region, which would be required for the connector 319, would increase the risk of damaging the cartridge holder in this region or even render it unmoldable. Thus, the shortened needle connector is advantageous.

Although the depicted embodiment shows only one fixing feature, a sloped surface may also be provided in case a plurality of fixing features is used. In the following embodiment, the sloped surface is not shown, however.

In FIGS. 2A and 2B a cartridge holder 302 with two integrated fixing features 322 is shown. The fixing features 322 are oppositely disposed where each fixing feature has a fixing surface 324 which is arranged to abut the cartridge surface 313, which may be formed flange-like. Two openings 325 are provided in the distal end wall 315 of the cartridge holder which interrupt the ring-like shape of the cartridge holder at positions which angularly and/or radially correspond to the position of the fixing surface 324 of the respective fixing feature. The respective opening 325 may be connected to the central opening 316. As explained previously, this assists in integrating the fixing feature into the cartridge holder by injection molding which is particularly easy and a low-cost process, suitable for high volumes. The disclosure above regarding the opening therefore also applies for this embodiment. Still further, more than two fixing features could be provided as well. In FIG. 2B, the needle connector overlaps axially with the fixing feature(s) 322.

As the fixing feature 322 interacts with the head portion in the depicted embodiments, cartridges with differently shaped main body portions may be secured in the cartridge holder easily, e.g. cartridges of different volumes, such as 1.5 mL and 3 mL, different diameters and/or lengths. The head portions of the cartridges may be formed alike.

It should be appreciated that the present disclosure is particularly advantageous for cartridge assemblies with cartridges which are permanently secured therein as cartridge units. However, also cartridge holders with removable cartridges where the cartridge can be replaced in the cartridge holder can be used as cartridge units in the presently disclosed concepts.

Cartridges of different volumes may have different lengths and/or different inner and/or outer diameters. The cartridge assembly may be a disposable item, which is, e.g. sold in the pharmacy. Different cartridges of the same or of different volumes may contain different drugs or drug formulations. Cartridges of a smaller volume may have a higher concentration of a drug. If the drug is insulin or an insulin derivative, for example, the cartridge of a smaller volume may have a concentration which is more than 2 times, e.g. 3 times the concentration of drug or medicament in the larger volume cartridge. The drug in the larger volume cartridge may be formed by the same active pharmaceutical ingredient. Differences in the content between the cartridges may be, preferably only, in the concentrations of the drug within the liquid, i.e. in the specific formulation of the drug. For example, a 3 mL cartridge may comprise 300 IU (IU: International Unit), e.g. of insulin, whereas the 1.5 mL cartridge may comprise 450 IU, which, taking into according the lower volume, corresponds to three times the concentration of drug in the 3 mL cartridge.

In reusable drug delivery devices, where the same drive mechanism can be used in conjunction with several cartridges, it is extremely advantageous to ensure that only cartridges with a specific drug or drug formulation can be operatively connected to the drive mechanism, e.g. connected to a housing within which the drive mechanism or elements thereof are retained. This is, sometimes, achieved by so-called coding or dedication systems or mechanisms. These systems or mechanisms may comprise features which are adjusted such that in a set of two drug delivery devices, each comprising a housing with a dose setting and/or drive mechanism and a cartridge unit releasably connected to the housing, where the two cartridge units have different drugs, drug formulations and/or dimensions, the respective cartridge unit can only be connected to the housing of one device and not to the housing of the other device.

An embodiment for a codable or dedicatable interface between a cartridge unit or cartridge assembly and a housing is described in conjunction with FIGS. 3A through 3D below.

Figure 3B:
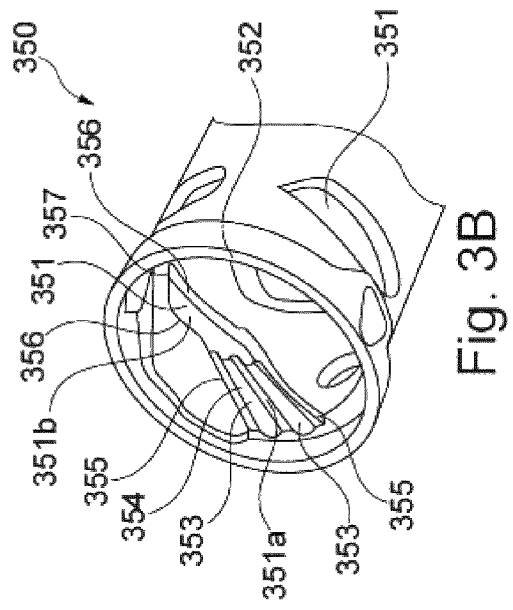
FIGS. 3A through 3D illustrate embodiments of potential coding structures using a schematic perspective view of a part of a cartridge unit in FIG. 3A, a schematic perspective view of a housing or housing part in FIG. 3B which is coded or matched to the unit in FIG. 3A, another schematic perspective view of a part of a cartridge unit in FIG. 3D, which is not matched or coded to the housing in FIG. 3B, and examples of potential cartridge unit coding structures which are incompatible with housing coding structures matching the other cartridge unit coding structures in FIG. 3C.
Figure 3D:
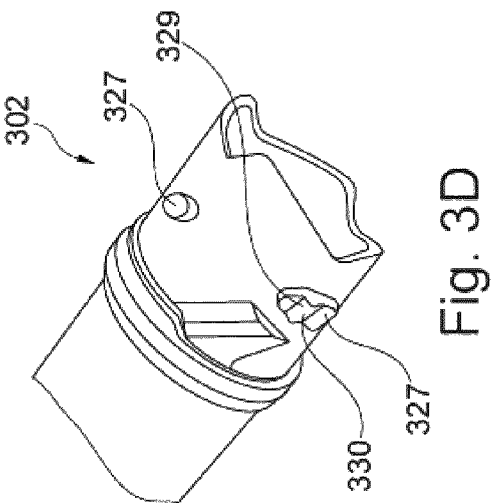
Figure 3A:
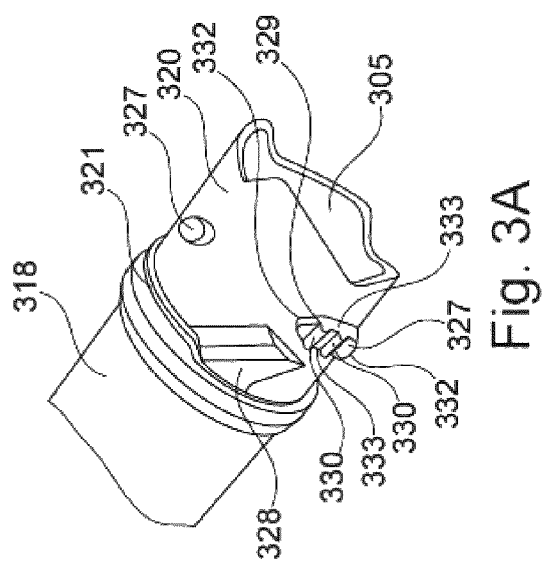

FIG. 3A shows a more detailed view of the proximal section of a cartridge holder 302, e.g. one of the holders described previously. Particularly, the connection region or interface region 320 is shown. In this region, one or more features which are adjusted to interact with features in a housing when connecting the cartridge holder 302 or the cartridge assembly 300 to the housing to form a drug delivery device. In particular, in the connection or interface region 320, one guide feature 327 or a plurality of guide features 327 are arranged. Different guide features 327 may be axially aligned and angularly separated from one another. The guide features 327 may guide movement of the cartridge holder 302 relative to the housing during assembling to the housing.

The cartridge holder 302 may, in particular in the connection or interface region 320, comprise a securing or detent feature 328. A plurality of securing features 328, where only one of them is shown, may be provided which are preferably uniformly disposed in the angular direction with respect to one another, e.g. diametrically opposite with respect to one another. Furthermore, preferably also in the connection or interface region 320, an interface or coding structure 329 is provided.

The respective guide feature may be realized as a lug protruding from the cartridge holder 302. The securing feature 328 may have a helical shape or extension. The coding structure may be realized by one or more interface features 330, e.g. protrusions. The respective interface feature 330 is restricted axially and angularly to the guide feature 327. The respective interface feature 330 may extend helically. The helix angle or the lead defined by the helix of the protrusion may correspond to the helix angle or the lead of the securing feature 328. The securing feature 328 and the interface feature may define a helix of the same helix angle or lead or even be arranged on a helix of the same helix angle or lead, which is formed by continuing the interface feature helically. The helix angle may be defined by the angle defining the constant slope of the helix with respect to a plane perpendicular to the main axis of the helix, which axis, in the present case, may be the main longitudinal axis of the cartridge holder.

Within the housing to which the cartridge holder is coded a complementary housing coding structure 354 is formed by housing interface features 353 which are, preferably, shaped in a way complementary to the shape of the cartridge unit interface features 330. The coding structures are expediently unique, such that cartridge units with specific drugs, drug formulations, and/or cartridge dimensions can only be attached to housings having a housing coding structure matching the cartridge unit coding structure. A housing part 350 of a housing which is adjusted, dedicated or coded to the cartridge holder in FIG. 3A is shown in FIG. 3B. The housing part 350 may be integrally formed with an (outer) housing of a drug delivery device as explained later on or as an additional component mounted in or at the housing. The housing part 350 comprises at least one, preferably a plurality of housing guide features 351. The housing guide feature 351 may be a track. The housing guide feature 351 comprises two different sections, a first section 351a and a second section 351b. The first section 351a extends at least predominantly axially, such as only axially or helically. The axial distance between two opposite ends of the section may be greater than the angular extension of the first section. For example the midpoints of the respective end can be taken as reference points for measuring the distances separating the ends. The housing part 350 has a distal end 352. Before the cartridge holder 302 is assembled to the housing part 350, the distal end 352 may face the cartridge unit. The housing part 350 may be hollow, e.g. formed sleeve-like in order to enable components of the drive mechanism and/or of the cartridge assembly to be received within an opening of the sleeve member or to travel through the opening. The section 351a is expediently arranged closer to the distal end of the device or the housing than the second section 351b of the housing guide feature 351. The second section 351b of the guide feature 351 may extend at least predominantly angularly, such as only angularly or helically. Particularly, the axial distance between opposite ends of the second section may be less than the angular extension of the second section. The axial distance the cartridge holder is moved in the first section may be greater than the axial distance it is moved in the second section. Alternatively or additionally, the angular distance the cartridge holder is moved in the first section may be less than the angular distance it is moved in the second section. The axial distance the cartridge holder is moved in the second section may be less than or equal to 1 mm, e.g. less than or equal to 0.5 mm. The guiding interface may be a bayonet-type interface.

In the depicted embodiment, the first section 351a extends helically or is configured to define a helical interface. The second section 351b may extend only angularly or helically or be configured to define a helical interface. However, the lead and/or pitch of helix of the second helical section 351a or the helical interface which is established while the guide feature travels within the second section may be smaller than the one of the first helical section 351a. In other word, the helix angle of the helix associated with the second section may be less than the one associated with the first section. Alternatively or additionally, the helixes which define the helical extension of the respective sections 351a and 351b or the associated helical interface may be oriented in opposite directions, e.g. they may be oppositely handed. In this way, in the second section, the cartridge holder may travel in the distal direction relative to the housing, i.e. opposite to the axial direction it travels in when the movement is guided in the first section.

Thus, the first and second sections define different stages of movement which is formed when the housing and cartridge unit guide features cooperate to form the guiding interface. The housing interface features are preferably arranged in the first section, e.g. only in the first section. When connecting the cartridge holder 302 to the housing part 350, the guide feature 327 is received in the distal end of the first section 351a of the associated housing guide feature 351. Within the first section 351a of the housing guide feature 351, the housing interface features 353 are provided, which are, preferably radially offset from guiding surfaces of the first section 351a. Accordingly, guiding surfaces such as angular surfaces 332 of the guide feature 327 of the cartridge holder can interact with the guiding surfaces 355 in the first section 351a of the housing guide feature to guide the helical movement of the cartridge holder relative to the housing part 350. The interface features 330 and 353 are helically oriented along a helix with a helix angle corresponding to the helix angle of the helix governing the helical movement of the guide features 327 of the cartridge holder relative to the housing. The number, pattern, and/or width of the interface features 330 and 353 is chosen such that the interface features 330 are received in the interface features 353, if the cartridge holder is dedicated or coded to the housing or housing part 350. Then, the unit can be attached to the housing part. In a non-dedicated unit, non-matching cartridge unit interface features 330 are applied. Thus, if a non-matching or non-dedicated unit is attempted to be connected to the housing part 350, the non-matching interface features block further axial or helical movement of the cartridge unit relative to the housing part 350. Expediently, the housing coding structure 354 is integrated into the first section 351a of the housing guide feature 351. Accordingly, if a non-matching cartridge unit is tried to be assembled to the housing or housing part, the user recognizes already at the beginning of the operation, i.e. before he has moved the cartridge holder axially to a considerable extent, that the cartridge unit is not matched to or not suitable for the housing. If a matching cartridge holder is attempted to be connected to the housing part 350 in FIG. 3B, however, such as the cartridge holder depicted in FIG. 3A, the cartridge unit and housing coding structures permit that helical travel is achieved in the first section. For doing so, the helical interface established by the interface features 330 and 353 has helix angle which corresponds to the one of the helical movement or helical interface defined by the guide features in the section where both interfaces are established, e.g. the first section 351a. The coding structure 354 of the housing part 350 is expediently restricted to a limited extent within the guide feature 351. Preferably, the second section 351b is free of a coding structure. In this way, once the second section 351b has been reached by the guide feature 327, free travel is permitted without any further interface in addition to the guiding interface. In the second section, one or more, preferably oppositely disposed, axial surfaces 333 of the guide feature 327 may interact with guiding surfaces 356 of the housing guide feature 351. Within this section, e.g. when the guide feature 327 abuts a rotational stop face 357 of the housing guide feature 351, the securing feature 328 may interact with a corresponding securing feature, i.e. a detent feature, in the housing to secure the cartridge holder to the housing. Before that the stop is established, the cartridge holder may be moved axially away from the housing to provide a defined initial position and/or to couple elements of the drive mechanism in the housing to provide an accurate first dose. A mechanism which has an initial proximal movement of the cartridge holder towards the housing which is followed by a distal movement away from the housing is disclosed in WO 2012/130704 A1, the entire disclosure content of which is herewith incorporated by reference into the present application. However, the proposed concepts are applicable to other reusable drug delivery devices as well, e.g. to injection devices such as pen-type injectors.

FIG. 3D shows a cartridge holder 302 which essentially corresponds to the one described in conjunction with FIG. 3A. However, this cartridge holder is incompatible with the housing part 350 in FIG. 3B due to the differently configured interface feature 330. Accordingly, the cartridge unit coding structure 329 does not match with the housing coding structure 354 and connecting this cartridge holder, which preferably holds a cartridge with a drug or drug formulation which is not designed to be dispensed with and/or of a dimension not suitable for the drive mechanism retained in the housing or the housing part 350, is prevented from being attached to the housing part 350.

In drug delivery devices, the drive mechanisms or housings of different devices may have to be tailored to the drug or drug formulation, and/or the volume of liquid contained in the cartridge unit and/or to the dimensions of the cartridge of the unit. Accordingly, it is advantageous that not only different cartridge units cannot be connected to one specific housing but also that different housings with different drive mechanisms cannot be connected to cartridge units containing the same drugs, drug formulations, volumes of liquid and/or cartridges of the same dimensions. Therefore, matching housings and cartridge units may be uniquely coded to one another.

The guiding interface established by the guide features 351 and 327 in the first section 351a of the guide feature 351 is a helical interface as is the further interface established by the interface features 330 and 352. The helix angles or leads of both interfaces may be equal. The helix angles or leads of the helical interfaces—the first section of the guiding interface and the further interface—may be equal even for two different cartridge units with different coding structures or interface features. Thus, a helical guiding interface of the same pitch or lead may be used in a variety of housings which are dedicated to different cartridge units and thus have different coding structures or interface features. Consequently, the cartridge unit guide features may be configured and arranged alike, even in differently coded cartridge units. Thus, although two cartridge units may contain different drugs or drug formulations and/or cartridges of different dimensions, the movements, particular the sequence of different movements, during connection of the cartridge holders to the housing may be the same. This is, for example, apparent from comparing FIGS. 3A and 3D which have different coding structures 329 but the same guide features 327. Aside from the different coding structures the cartridge holders may be have the same dimensions and configurations.

All of the cartridge guide features 327, only one of the guide features 327 or only a part of the guide features of a particular cartridge unit may be provided with cartridge unit interface features. The number of housing guide features which are provided with a housing coding structure may be greater than the number of cartridge unit guide features provided with a cartridge unit coding structure. Thus, the cartridge unit can be assembled to the housing in different rotational orientations and proper coding is achieved in every rotational orientation.

Figure 3C:
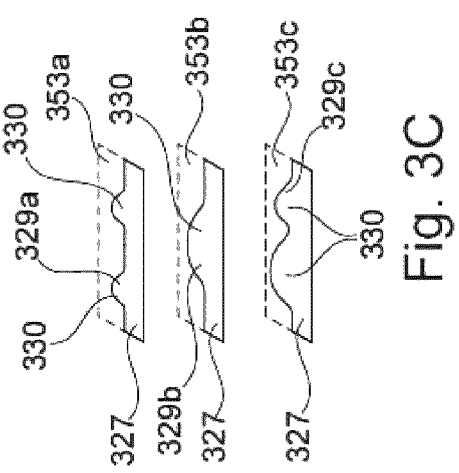

FIG. 3C shows different possible coding structures (329a through 329c) which are unique due to width, number, angular pitch, and/or position of the interface features 330 forming the coding structure. The structure 329a on the top has two interface features 330 of equal width. This structure is employed in FIGS. 3A and 3B. As compared to the structure 329a, the structure 329b in the middle has one interface feature but of greater angular width and at a different angular position on the guide feature 327. The lowermost structure 329c has two interface features of different angular widths. These coding structures are compatible only with housing coding structures having interface features of complementary shapes—illustrated by the dashed lines—but incompatible with housing coding structures matching the other cartridge unit coding structures. Thus, cartridge units having one of these coding structures 329 a to c can only be attached to housings having a matching housing coding structure 353a to c and not to housings having a different housing coding structure, where the respective housing coding structure is selected from the structures complementary to the ones shown in FIG. 3C. Nevertheless, all of the guide features 327 may be suitable to establish a helical interface of the same lead. Further the interface features of the different coding structures and/or the ones of the same coding structure, if a plurality of interface features are provided, may have or may define the same helix angle or a helix of the same lead. The respective helix or helix angle, expediently, corresponds to the one defined by the first section 351a of the housing guide feature.

Of course, instead of being lugs or protrusions as shown in the embodiments, the cartridge unit interface features 330 could be realized as recesses and/or the cartridge unit guide features could be realized as recesses. The housing interface features and/or the housing guide features do expediently have the complementary shape or structure, e.g. lugs or protrusions.

Figure 4:
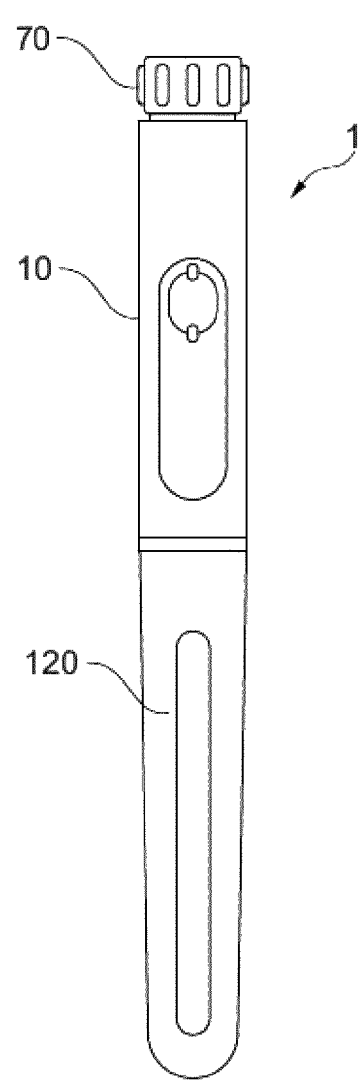
FIG. 4 illustrates an embodiment of a drug delivery device with a cap covering the distal end of the device prior to a dose setting operation.
Figure 5:
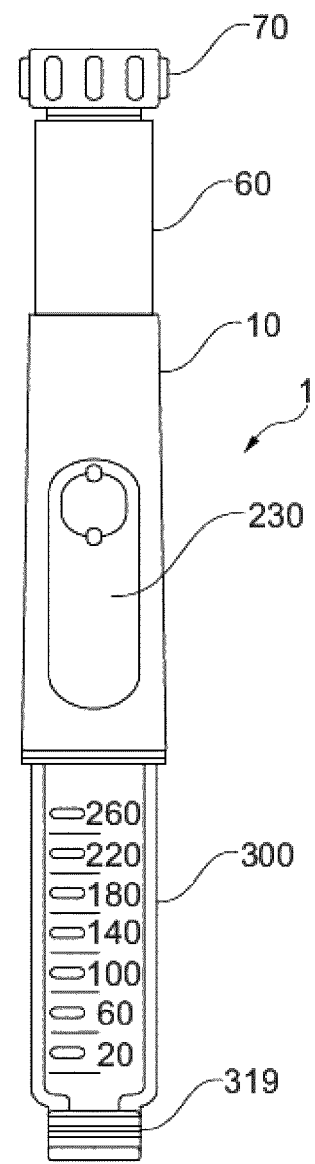
FIG. 5 illustrates the device of FIG. 4 where the cap has been removed to uncover the distal end of the cartridge assembly or unit.

FIGS. 4 and 5 schematically illustrate embodiments of a drug delivery device suitable to be used in conjunction with the disclosed cartridge assemblies or coding systems or mechanisms. FIG. 4 shows the device 1 in a condition where a cap 120 is attached and covers the cartridge assembly 300 or unit. In FIG. 5 the cap has been removed. The cartridge assembly 300 is, expediently releasably, connected to a main body or housing 10 of the drug delivery device 1 as depicted in FIG. 5. The housing expediently defines the outer contour of the device and may be formed sleeve-like. The housing part 350 may be retained in the interior of housing 10. A needle unit can be connected to the needle connector 319 in order to dispense drug or medicament from the device 1. A dose setting member 70 is movably retained in the housing 10 and can be manipulated by the user to set a dose. For example, it can be rotated relative to the housing to set a dose. The device may be a variable dose device, where the size of the dose is not predetermined by the design of the drive mechanism retained in the housing but rather may be changed by the user. In FIG. 5, a dose set condition of the drug delivery device is illustrated, where the numeral depicted in window 230 is changed as compared to FIG. 4 such that it illustrates the size of the currently set dose. The device may be designed such that during dose setting, the dose setting member 70 is displaced proximally relative to the housing 10. Alternatively, the dose setting member may stay in the same axial position independently of the set dose. From the position depicted in FIG. 5, a dispensing action may be initiated, expediently by moving or exerting a force in the distal direction onto the dose setting member 70 or a dose dispensing member provided in a proximal end section of the drug delivery device 1. To dispense the dose, the bung is displaced distally relative to the cartridge, e.g. by a piston rod of the device (not explicitly shown).

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

REFERENCE NUMERALS 300 cartridge assembly
301 cartridge
302 cartridge holder
303 cartridge retaining section
304 inner wall
305 opening
306 dispensing end
307 drug
308 septum
309 septum retainer
310 head portion
311 main body portion
312 neck portion
313 cartridge surface
314 shoulder surface
315 distal end wall
316 opening
317 distal region
318 main body region
319 needle connector
320 connection region
321 step
322 fixing feature
323 injection gate mark
324 fixing surface
325 opening
326 surface
327 guiding feature
328 securing feature
329 coding structure
329a-c coding structure
330 interface feature
331 shoulder region
332 angular surface
333 axial surface
340 cartridge body
341 reinforcement section
342 cartridge support features
350 housing part
351 housing guide feature
351a, b section
352 distal end
353 housing interface feature
354 coding structure
355 guiding surface
356 guiding surface
357 stop
1 drug delivery device
120 cap
70 dose setting member
10 housing
230 window
A thickness
B distance

The invention claimed is:

1. A cartridge unit for a drug delivery device, comprising:
a cartridge unit guide feature, the cartridge unit guide feature being provided to mechanically cooperate with a housing guide feature provided on a housing of the drug delivery device to establish a guiding interface in order to guide relative movement of the cartridge unit and the housing when attaching the cartridge unit to the housing,
wherein the cartridge unit guide feature is provided with at least one cartridge unit interface feature, wherein the at least one cartridge unit interface feature is adapted to establish a further interface with the housing,
wherein the cartridge unit is a cartridge assembly comprising a cartridge and a cartridge holder, wherein the cartridge is permanently secured in the cartridge holder,
wherein the cartridge comprises a head portion, a main body portion, and a neck portion, wherein the neck portion is arranged between the head portion and the main body portion, and wherein the neck portion has a reduced diameter as compared to the main body portion and the head portion,
wherein the cartridge unit guide feature is provided on the cartridge holder,
wherein the guiding interface is configured to define a first stage of movement and a second stage of movement, wherein the first stage of movement precedes the second stage of movement when attaching the cartridge unit to the housing, wherein the further interface is established in the first stage of movement and released in the second stage of movement, wherein the further interface comprises a helical interface, wherein a lead of a helical movement guided by the helical interface is equal to a lead of a helical movement of the cartridge unit relative to the housing during the first stage of movement, and wherein the further interface and the guiding interface are different interfaces.

2. The cartridge unit of claim 1, wherein the at least one cartridge unit interface feature is provided on a radially facing surface of the cartridge unit guide feature.

3. The cartridge unit of claim 1, wherein the at least one cartridge unit interface feature is provided on a radially facing surface of the cartridge unit guide feature, and wherein the cartridge unit guide feature is a radially oriented protrusion.

4. The cartridge unit of claim 1, wherein the at least one cartridge unit interface feature is a protrusion or a recess extending along the cartridge unit guide feature.

5. The cartridge unit of claim 1, wherein the at least one cartridge unit interface feature is an independent feature from the cartridge unit guide feature.

6. The cartridge unit of claim 1, wherein the at least one cartridge unit interface feature is angularly restricted to a region between two angularly facing surfaces of the cartridge unit guide feature, the two angularly facing surfaces facing in opposite angular directions.

7. The cartridge unit of claim 1, wherein the at least one cartridge unit interface feature is axially restricted to a region between two axially facing surfaces of the cartridge unit guide feature, the two axially facing surfaces facing in opposite axial directions.

8. The cartridge unit of claim 1, wherein the guiding interface is configured such that the cartridge unit is moved relative to the housing in the second stage of movement in an axial direction opposite to an axial direction that the cartridge unit is moved relative to the housing in the first stage of movement.

9. The cartridge unit of claim 1, wherein the cartridge unit is releasably attached to the housing of the drug delivery device through an interaction of the at least one cartridge unit interface feature and a housing interface feature of the housing.

10. A set comprising a first cartridge unit and a second cartridge unit, wherein the first cartridge unit comprises:

a first cartridge unit guide feature, the first cartridge unit guide feature being provided to mechanically cooperate with a first housing guide feature provided on a first housing of a first drug delivery device to establish a first guiding interface in order to guide relative movement of the first cartridge unit and the first housing when attaching the first cartridge unit to the first housing, wherein the first cartridge unit guide feature is provided with a first cartridge unit interface feature, wherein the first cartridge unit interface feature is adapted to establish a first further interface with the first housing, wherein the first cartridge unit is a first cartridge assembly comprising a first cartridge and a first cartridge holder, wherein the first cartridge is permanently secured in the first cartridge holder, wherein the first cartridge comprises a first head portion, a first main body portion, and a first neck portion, wherein the first neck portion is arranged between the first head portion and the first main body portion, and wherein the first neck portion has a reduced diameter as compared to the first main body portion and the first head portion, wherein the first cartridge unit guide feature is provided on the first cartridge holder, wherein the first guiding interface is configured to define a first stage of movement and a second stage of movement, wherein the first stage of movement precedes the second stage of movement when attaching the first cartridge unit to the first housing, wherein the first further interface is established in the first stage of movement and released in the second stage of movement, wherein the first further interface comprises a first helical interface, wherein a lead of a helical movement guided by the first helical interface is equal to a lead of a helical movement of the first cartridge unit relative to the first housing during the first stage of movement, and wherein the first further interface and the first guiding interface are different interfaces;

wherein the second cartridge unit comprises:

a second cartridge unit guide feature, the second cartridge unit guide feature being provided to mechanically cooperate with a second housing guide feature provided on a second housing of a second drug delivery device to establish a second guiding interface in order to guide relative movement of the second cartridge unit and the second housing when attaching the second cartridge unit to the second housing, wherein the second cartridge unit guide feature is provided with a second cartridge unit interface feature, wherein the second cartridge unit interface feature is different from the first cartridge unit interface feature, wherein the second cartridge unit interface feature is adapted to establish a second further interface with the second housing, wherein the second cartridge unit is a second cartridge assembly comprising a second cartridge and a second cartridge holder, wherein the second cartridge is permanently secured in the second cartridge holder, wherein the second cartridge comprises a second head portion, a second main body portion, and a second neck portion, wherein the second neck portion is arranged between the second head portion and the second main body portion, and wherein the second neck portion has a reduced diameter as compared to the second main body portion and the second head portion, wherein the second cartridge unit guide feature is provided on the second cartridge holder, wherein the second guiding interface is configured to define a first stage of movement and a second stage of movement, wherein the first stage of movement precedes the second stage of movement when attaching the second cartridge unit to the second housing, wherein the second further interface is established in the first stage of movement and released in the second stage of movement, wherein the second further interface comprises a second helical interface, wherein a lead of a helical movement guided by the second helical interface is equal to a lead of a helical movement of the second cartridge unit relative to the second housing during the first stage of movement, and wherein the second further interface and the second guiding interface are different interfaces.

11. The set of claim 10, wherein the first cartridge unit contains a first drug or drug formulation, and the second cartridge unit contains a second drug or drug formulation, wherein the second drug or drug formulation is different from the first drug or drug formulation.

12. The set of claim 10, wherein the first cartridge has a first size, and the second cartridge has a second size that is different from the first size.

13. The set of claim 10, wherein the first cartridge unit guide feature and second cartridge unit guide feature have the same configuration.

14. The set of claim 10, wherein a width, a number, or a pitch of the first cartridge unit interface feature of the first cartridge unit is different from the respective width, number, or pitch of the second cartridge unit interface feature of the second cartridge unit.

15. A drug delivery device comprising the cartridge unit of claim 1.

16. The drug delivery device of claim 15, wherein the cartridge unit contains a medicament.

17. A method comprising:
dispensing a dose of medicament from a cartridge that is permanently secured in a cartridge holder of a cartridge unit for a drug delivery device,
wherein the cartridge unit comprises:
a cartridge unit guide feature, the cartridge unit guide feature being provided to mechanically cooperate with a housing guide feature provided on a housing of the drug delivery device to establish a guiding interface in order to guide relative movement of the cartridge unit and the housing when attaching the cartridge unit to the housing,
wherein the cartridge unit guide feature is provided with at least one cartridge unit interface feature, wherein the at least one cartridge unit interface feature is adapted to establish a further interface with the housing,
wherein the cartridge unit is a cartridge assembly comprising the cartridge and the cartridge holder,
wherein the cartridge comprises a head portion, a main body portion, and a neck portion, wherein the neck portion is arranged between the head portion and the main body portion, and wherein the neck portion has a reduced diameter as compared to the main body portion and the head portion,
wherein the cartridge unit guide feature is provided on the cartridge holder,
wherein the guiding interface is configured to define a first stage of movement and a second stage of movement, wherein the first stage of movement precedes the second stage of movement when attaching the cartridge unit to the housing, wherein the further interface is established in the first stage of movement and released in the second stage of movement,
wherein the further interface comprises a helical interface, wherein a lead of a helical movement guided by the helical interface is equal to a lead of a helical movement of the cartridge unit relative to the housing during the first stage of movement, and
wherein the further interface and the guiding interface are different interfaces.

* * * * *